(12) United States Patent
Pritzke

(10) Patent No.: US 8,650,974 B2
(45) Date of Patent: Feb. 18, 2014

(54) DEVICE FOR COLLECTING SAMPLES FROM A POWDER STREAM

(75) Inventor: Heinz Pritzke, Braunsdorf (DE)

(73) Assignee: Glatt Systemtechnik GmbH, Land (DE)

(*) Notice: Subject to any disclaimer, the term of this patent is extended or adjusted under 35 U.S.C. 154(b) by 374 days.

(21) Appl. No.: 13/138,318

(22) PCT Filed: Feb. 23, 2011

(86) PCT No.: PCT/EP2011/052643
§ 371 (c)(1),
(2), (4) Date: Aug. 1, 2011

(87) PCT Pub. No.: WO2011/113670
PCT Pub. Date: Sep. 22, 2011

(65) Prior Publication Data
US 2012/0055270 A1 Mar. 8, 2012

(30) Foreign Application Priority Data
Mar. 17, 2010 (DE) .................. 10 2010 011 724

(51) Int. Cl.
*G01N 1/20* (2006.01)
*G01N 1/16* (2006.01)
*G01N 1/12* (2006.01)

(52) U.S. Cl.
USPC .................. 73/863.81; 73/863.82; 73/864.51

(58) Field of Classification Search
USPC ......... 73/863.51–54, 863.81, 863.82, 863.85, 73/864, 864.31, 864.33, 864.51
See application file for complete search history.

(56) References Cited

U.S. PATENT DOCUMENTS

| 1,966,712 A | | 7/1934 | Fisher et al. | |
| 2,683,373 A | * | 7/1954 | Gallup et al. | 73/863.53 |
| 3,066,539 A | | 12/1962 | Coker et al. | |
| 3,614,230 A | | 10/1971 | Crawford | |
| 3,949,614 A | * | 4/1976 | Abonnenc | 73/863.83 |
| 4,024,765 A | * | 5/1977 | Abonnenc | 73/863.83 |
| 4,625,570 A | * | 12/1986 | Witherspoon et al. | 73/863.81 |

(Continued)

FOREIGN PATENT DOCUMENTS

| DD | 160734 A3 | 2/1984 |
| DE | 2456643 A1 | 10/1975 |
| EP | 1992933 A1 | 11/2008 |
| JP | 7110291 A | 4/1995 |

OTHER PUBLICATIONS

"SamFreeGlide": "The only in-line Powder Sampler guaranteed not to jam"; Kersting GmbH Sampling & Grounding; 2009.

*Primary Examiner* — Hezron E Williams
*Assistant Examiner* — Nathaniel Kolb
(74) *Attorney, Agent, or Firm* — Jacobson Holman PLLC

(57) ABSTRACT

The invention relates to a device for collecting samples from a powder stream guided in a powder line (3). The device comprises a housing (1) that is disposed on the powder line (3), a slide (5) which comprises a sample well (13) disposed upwardly relative to the powder stream, and a pushing device. There is a sample container (18) provided that matches the sample well (13). An associated withdrawal device (19) comprising withdrawal tongs (20) can be inserted into the housing (1) in such a way that the withdrawal tongs (20) are located axially above the sample well (13) in the inoperative position of the slide (5) and can be fitted on the sample container (18) and connected to the same.

8 Claims, 4 Drawing Sheets

(56) References Cited

U.S. PATENT DOCUMENTS 4,655,371 A    4/1987   Ingleby
4,702,114 A * 10/1987   Cabannes .................. 73/863.85
4,771,642 A    9/1988   Parth et al.
5,319,987 A    6/1994   Vassel

* cited by examiner

DEVICE FOR COLLECTING SAMPLES FROM A POWDER STREAM

This is a national stage of PCT/EP2011/052643 filed Feb. 23, 2011 and published in German, which claims the priority of German number 10 2010 011 724 filed Mar. 17, 2010, hereby incorporated by reference.

The invention relates to a device for collecting samples from a particularly free-falling stream of powder or granular material, referred to hereinafter in short as "powder stream". The product samples are required particularly for examining the actual mixing ratios and the homogeneity of a mixed product comprising at least two individual powdery or granular substances particularly for pharmaceutical or chemical applications.

Various devices for collecting product samples from a free-falling powder stream are disclosed in the prior art. In practice, the product samples are collected in these devices at regular intervals, in most cases, within a production cycle for the purpose of examining predetermined parameters.

The present invention relates to a device of the type corresponding to the in-line powder sampler "SamFreeGlide" of the Kerting [sic: Kersting] GmbH company, Brilon (Germany)—(http://www.kersting-ind.de/de/produkte/probenahme/inline-probenehmer/schuettgut-probenehmer/samfreeglide.html). The in-line powder sampler is flange-mounted on the pipe conveying bulk material. A sampling cup disposed on a supporting rod is mounted inside the in-line powder sampler in the inoperative position. A sealing plate that seals the interior of the in-line powder sampler from the pipe conveying bulk material is provided at the end of the supporting rod. For collecting a sample, the supporting rod comprising the sampling cup and the sealing plate is pushed manually or pneumatically into the interior of the pipe conveying bulk material and pulled back after the sampling cup is filled with the bulk material. Thereafter, the sampling cup is emptied over a container or a pipeline by rotating the supporting rod. The sample travels on a random path to the analysis station. In such a type of sampling process, the sample collected can be segregated, at least in part, when the sampling cup is emptied, and this can lead to erroneous analyses.

DE 2456643 A1 describes a volumetric sampler for taking samples of fluid substances, more particularly substances in granular or powdered form, in a testing area. The sampler is disposed radially on a conveying pipe and it comprises a finger comprising a coaxial sleeve (closure member), in which a cylindrical probe is guided axially. The probe comprises a recess, in which a predetermined volume of a substance flowing in the conveying pipe can be collected. By means of an axial movement, the recess can be moved both into the conveying pipe and outside the same above a hopper. After filling the probe in the conveying pipe, the probe can be removed by appropriate means axially from the conveying pipe and moved over a hopper. After rotating the probe so that the recess opens downwardly, the substance sample collected is emptied into the hopper.

It is thus an object of the present invention to provide a device for collecting samples from a stream of powder or granular material of the aforementioned type, in which device the samples cannot be segregated during their travel to the analysis station. A further object is to adapt the sample quantity to be collected, for example, 1 cm$^3$, 2 cm$^3$ or 4 cm$^3$, to suit the specific process cycle and to vary the location, at which the sample is collected from within the stream of granular material. Moreover, the device is intended to enable a cleaning of its interior without being disassembled.

This object is achieved by the invention by means of a device having the features defined in Claim 1. Advantageous developments of the invention are characterized in the sub-claims and are explained below in more detail together with the description of the preferred embodiment of the device with reference to the drawings.

According to the invention, a sample container is provided, in which the sample can be collected and brought to the analysis station without moving or shaking the sample itself.

In a manner known per se, the device comprises a housing that comprises an axis and that is disposed on the powder line so as to extend radially relative to the longitudinal axis of the powder line. The end face of the housing reaches up to the plane of the inner wall of the powder line so that the powder stream is not obstructed by interruptions inside the powder line. In this connection, it is immaterial as to whether the end face of the housing directly penetrates the wall of the powder line or whether a separate flange-like connecting piece is inserted into the wall of the powder line, and the housing is disposed on an outer flange of the connecting piece.

A slide is mounted for movement along the axis of the housing. In the inoperative position, the end face of the slide is likewise located so as to be flush with the inner wall of the powder line and the end face of the housing. A flat surface is provided on the circumference of the slide upwardly relative to the powder stream, which flat surface prevents a rotation of the slide relative to the housing. A sample well, into which the sample container can be inserted, is provided within this surface on the top side of the slide. A pushing device is provided that is well-suited to move the slide along the housing axis in such a way that the sample well together with the sample container can be moved into the powder stream.

The sample container comprises a top collar that is accessible inside the sample well, the collar of the sample container inserted into the sample well being approximately flush with the plane of the surface on the top side of the slide.

A withdrawal device comprising withdrawal tongs is provided as part of the device of the invention. The withdrawal device can be inserted together with the withdrawal tongs into the housing in such a way that the withdrawal tongs are located axially above the sample well in the inoperative position of the slide. The withdrawal tongs can engage the top collar of the sample container in such a way that the sample container can be inserted by the withdrawal tongs into the sample well or removed therefrom.

According to the invention, two spreadable segments are provided in the form of the withdrawal tongs at the bottom front end of the withdrawal device, which two spreadable segments comprise at least one step located centrally. Appropriately, a pressure rod is mounted for movement in the withdrawal device, at the bottom end of which pressure rod there is a pressure cone provided that bears against the step in the inoperative position. When the pressure rod moves downwardly, the pressure cone acts against the step, and the two spreadable segments are pushed apart in the manner of forceps. In the state in which the segments are spread apart, the withdrawal tongs can engage the collar located on the sample container.

The withdrawal device can be configured to be freely inserted manually through a withdrawal flange on the housing. In special cases, the withdrawal device can also be mechanized. For this purpose, a mechanical device or a device that is actuated pneumatically, hydraulically or electrically can be provided, by means of which the withdrawal tongs disposed on the withdrawal device can take hold of the sample container and manipulate the same into and out of the sample well.

Advantageously, there is a bottom opening provided on the housing, through which opening excess powder residue from the space surrounding the slide and the sample well can escape. This powder residue can be collected, for example, in a flange-mounted container.

Particularly for the use of the device in the pharmaceutical industry, high demands are placed on cleanliness of the device and its cleaning options. For this purpose, it is advantageous to connect the withdrawal flange to lines for supplying liquid and/or gaseous rinsing agents. Appropriately, the bottom opening disposed on the housing can be in the form of a rinsing flange that can be connected to a line for discharging the liquid and/or gaseous rinsing agents introduced by way of the withdrawal flange.

At times when there is no sampling carried out, it is advantageous to provide a cover on the withdrawal flange, which cover can seal the housing.

The device is explained below in more detail with reference to an exemplary embodiment. Accordingly, FIG. 1 is an overall view of a device of the invention disposed on a powder line.

Figure 1:
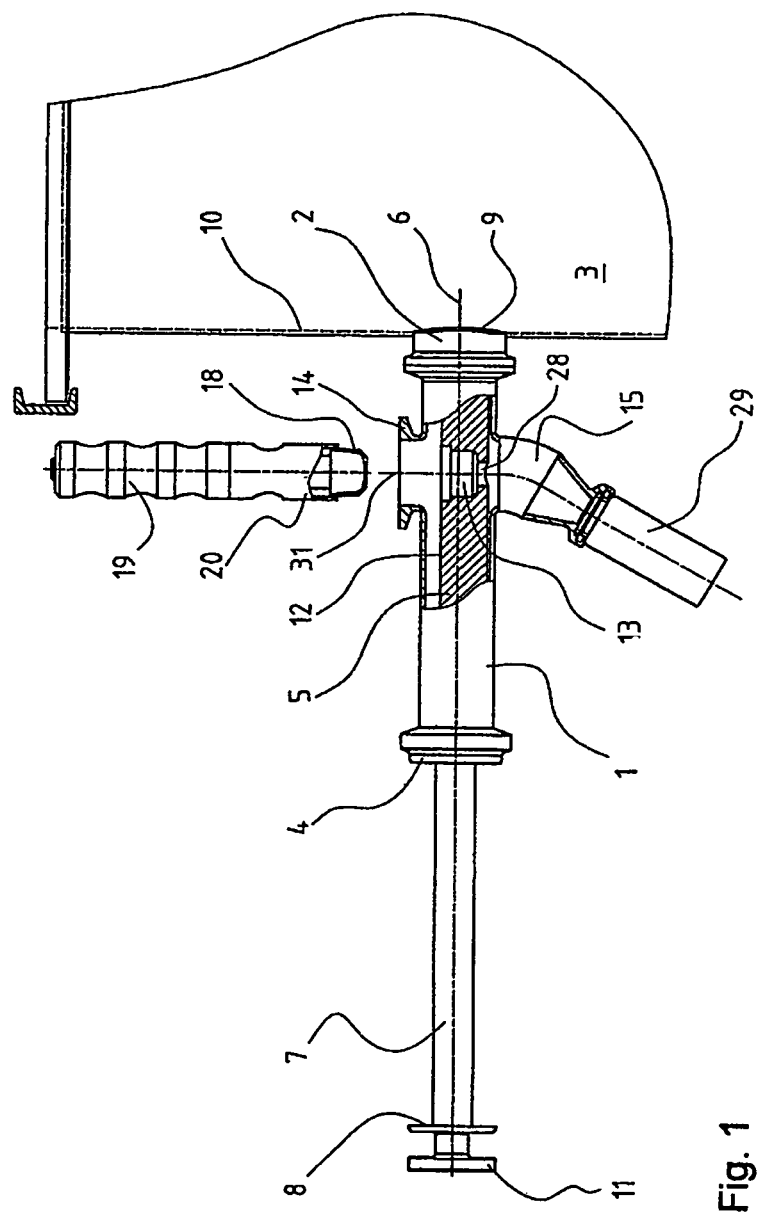
Figure 2:
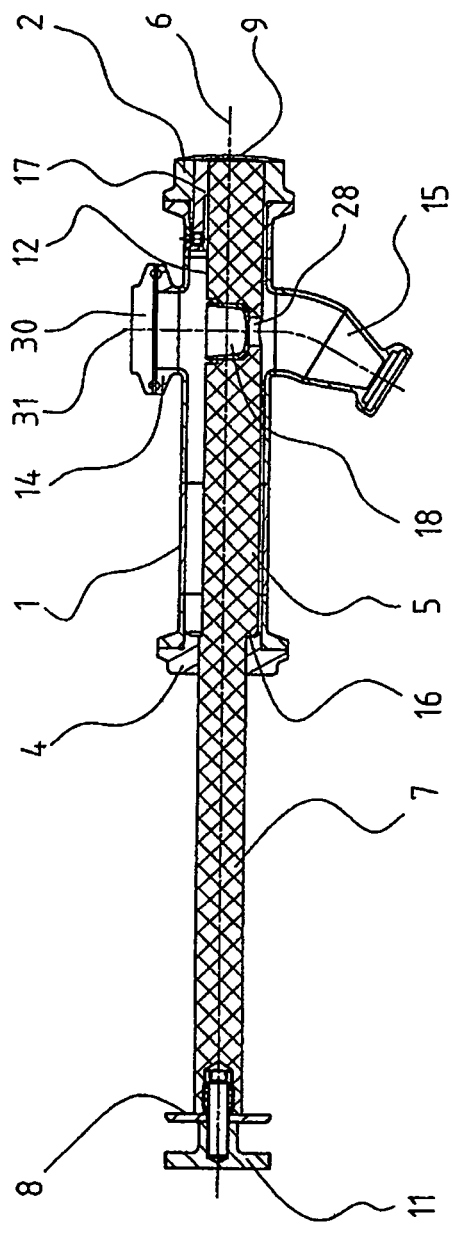
FIG. 2 shows the corresponding device in an isolated position and a cross-sectional view thereof.

FIG. 1 is an overall view and FIG. 2 is a cross-sectional view of a device of the invention. Here, the base body 1 is disposed on the wall of a powder line 3 by means of a flange 2. A bearing flange 4 is provided on the base body 1 opposite to the flange 2 in the axial direction. Within the base body 1, there is a slide 5 located that can be moved along the housing axis 6. The slide 5 is mounted in the flange 2 and in the bearing flange 4, the slide 5 being in the form of a push rod 7 in the region of the bearing flange 4 and outside the housing 1. At the region of the transition from the inner section of the slide 5 to the push rod 7, there is an inner stop collar 16 provided that bears against the bearing flange 4 in the inoperative position.

A grip element 11 comprising an outer stop washer 8 is provided on the push rod 7 in the exemplary embodiment shown. If necessary, a pneumatic or electromotive drive can also be provided instead of the grip element 11.

The path, along which the push rod 7 can move within the housing 1, is delimited on the one hand by the inner stop collar 16 and, on the other hand, by the outer stop washer 8, the stop collar 16 and the stop washer 8 striking against the bearing flange 4 on both sides thereof. When the slide 5 bears against the bearing flange 4 by means of the stop collar 16, the end face 9 of the slide 5 is located in the plane of the inner surface 10 of the powder line 3. This plane can be both a curved pipe surface and a flat surface of a box-shaped powder line.

The slide 5 is guided in the flange 2 by means of a surface 12 so as to be rotationally fixed. For this purpose, a corresponding anti-rotation element 17 is inserted in the flange 2. A sample well 13 comprising an opening 28 downwardly at the center is recessed into the top side of the slide 5, that is, into the surface 12.

On the housing 1, there is a withdrawal flange 14 provided at the top and a rinsing flange 15 that is located opposite thereto. The position of the vertical axis 31 of the withdrawal flange 14 corresponds to the position of the central axis extending through the sample well 13 when the stop collar 16 bears against the bearing flange 4.

A drip glass 29, in which excess powder residue from the space surrounding the slide 5 and the sample well 13 can be collected, is provided on the rinsing flange 15, for example.

According to the invention, a withdrawal device 19 comprising withdrawal tongs 20 is provided as part of the device in addition to the housing 1 comprising the slide 5. FIG. 1 shows a sample container 18 being held on the withdrawal tongs 20. The withdrawal device 19 in this exemplary embodiment is one that can be handled freely, that is, it is manually guided through the withdrawal flange 14 only for inserting and removing a sample container 18 into and from the sample well 13 respectively. On the withdrawal flange 14, it is possible to provide a cover 30, by means of which the housing 1 can be sealed during times when there is no sampling carried out.

Figure 3:
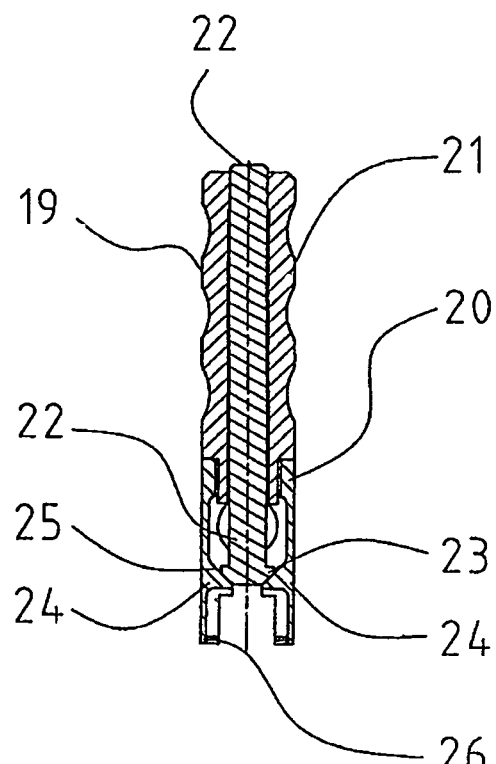
FIG. 3 shows an associated withdrawal device that can be handled manually.
Figure 4:
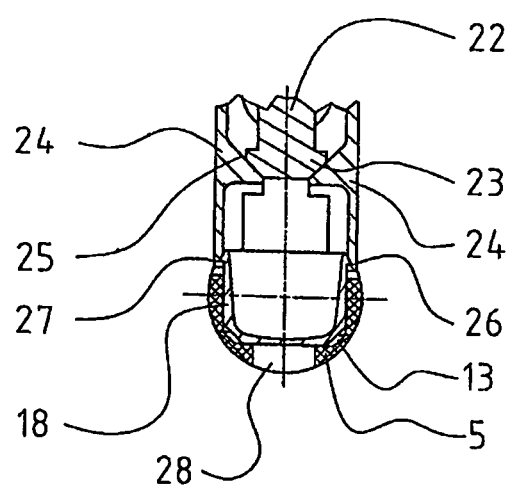
FIG. 4 is an enlarged view of the removal tongs disposed at the bottom end of the withdrawal device shown in FIG. 3, which removal tongs hold a sample container disposed inside the sample well.

FIGS. 3 and 4 are enlarged and partly enlarged views of the withdrawal device 19 respectively. The withdrawal device 19 comprises a handle 21 comprising downwardly disposed withdrawal tongs 20. A pressure rod 22 comprising a bottom pressure cone 23 is guided through the top end of the handle 21 and held here. Two elastic sections 24 are provided in the form of the withdrawal tongs 20. Internally, in the region of the two elastic sections 24, there is a collar-like step 25 located, against which the pressure cone 23 bears in the inoperative position. Notches 26 are located at the front ends of the elastic sections 24.

FIG. 4 shows the withdrawal tongs 20 in a position, in which they engage a top collar 27 of the sample container 18 in the sample well 13 by means of notches 26.

Figures 5A, 5B:
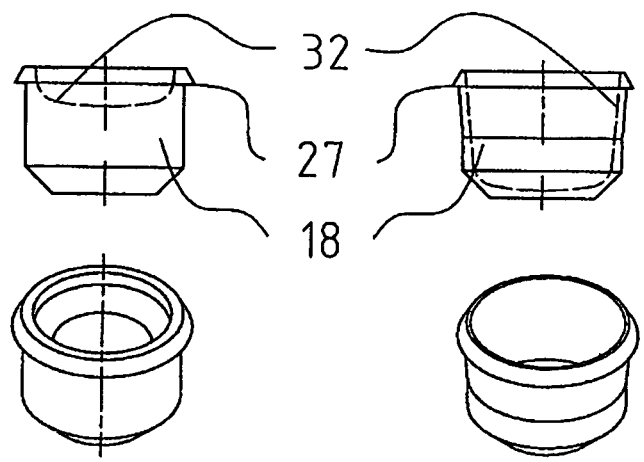
FIGS. 5a and 5b show sample containers having varying volumetric capacity.

FIGS. 5a and 5b each show a sample container 18, FIG. 5a showing a sample container 18 that has a volumetric capacity of, for example, 1 $cm^3$ and FIG. 5b showing a sample container 18 having a volumetric capacity of 4 $cm^3$. The interior of the sample containers is marked by a dashed line 32 in each case.

The sample containers 18 used in the device of the invention all have the same outer dimensions, but the inner space, that is, the amount of volumetric capacity of the sample container 18 can be adapted freely to meet the different technological requirements.

The front end of a sample container 18 inserted into the sample well 13 is located approximately in the plane of the surface 12 within the slide 5 so that the slide 5 together with the sample container 18 can be pushed through the flange 2 effectively.

In this exemplary embodiment, the sample container 18 is made of stainless steel, and the withdrawal tongs 20 comprising the two elastic sections 24 are made of polytetrafluoroethylene (PTFE). Thus both the elastic sections 24 are made of a resilient material and they can engage the collar 27 effectively.

If necessary, a grating or marking can also be provided on the push rod 7, by means of which grating or marking the sample container 18 can be made to assume a specific position within the powder line 3 when collecting samples. That is, powder can be collected, for example, from the border area or the center of the powder line 3 corresponding to technological specifications.

The application of the device for collecting samples is described below in more detail. A powder or granular material of a readily segregating product mixture is conveyed in free fall inside the powder line 3. According to specific technological specifications, samples are to be collected at regular intervals, and the mixing ratio as well as the homogeneity of the product mixture is to be examined.

For collecting the sample, a sample container 18 that has a volumetric capacity meeting the technological requirements is selected and held by means of the withdrawal tongs 20 disposed on the withdrawal device 19. When inserting a sample container 18 into the sample well 13, the withdrawal device 19 is fitted on the sample container 18 outside the device and pressed onto the same in such a way that the pressure rod 22 acts by means of its bottom pressure cone 23 against the collar-like step 25 disposed on the elastic sections 24, and the elastic sections 24 are pushed apart until the collar 27 of the sample container 18 snaps into place in the notch 26. The stroke of the pressure rod 22 required in practice is approximately 2 mm.

Thereafter, the withdrawal device 19 together with the sample container 18 is inserted through the withdrawal flange 14 into the housing 1, and the sample container 18 is inserted into the sample well 13. Then the elastic sections 24 are again spread apart by pressing the pressure rod 22, and the withdrawal device 19 is released from the sample container 18.

For collecting the sample, the slide 5 is moved along the housing axis 6 by means of the grip element 11 disposed on the push rod 7 until the stop washer 8 strikes against the bearing flange 4. In this position, the sample container 18 disposed in the sample well 13 is located centrally inside the free-falling powder stream in the powder line 3.

If necessary, the push rod 5 [sic: push rod 7] can also be pushed only up to a defined marking provided thereon that corresponds to the position of the sample container 18 at a radial distance from the center of the powder line 3.

In a short space of time, the sample container 18 is filled, and the slide 5 can be pulled back. In doing so, powder that is located above the sample container 18 is stripped off by the flange 2 so that the sample container 18 is filled exactly to its brim corresponding to its volume.

The slide 5 is pulled back again until the stop collar 16 bears against the bearing flange 4. The withdrawal device 19 is fitted on the sample container 18, and the withdrawal tongs 20 are spread apart by means of the pressure rod 22 until the collar 27 of the sample container 18 snaps into place in the notch 26. Thereafter, the withdrawal device 19 together with the full sample container 18 is removed through the withdrawal flange 14 and brought to the analysis station. If appropriate, it is also possible to collect a number of samples one after the other and bring the same collectively to the analysis station.

Irrespective of the sampling process, it is necessary, in practice, to clean the interior of the housing 1 comprising the slide 5 at regular intervals. For this purpose, a liquid and/or gaseous cleaning agent can be guided by means of the withdrawal flange 14 and through the housing 1 toward the rinsing flange 15.

Particularly in the application of the device in the pharmaceutical industry, the device is required to meet high standards of cleanliness. For such applications, the device can be connected appropriately to lines for the supply and discharge of cleaning agents. For example, the interior of the housing 1 extending from the withdrawal flange 14 to the rinsing flange 15 can be rinsed first with a liquid cleaning agent, and then with a drying gas. The device is then available in a very clean state for the next collection of a product sample of the same or another kind.

LIST OF REFERENCE NUMERALS OR CHARACTERS USED

1 Base body
2 Flange
3 Powder line
4 Bearing flange
5 Slide
6 Housing axis
7 Push rod
8 Stop washer
9 End face
10 Inner surface
11 Grip element
12 Surface
13 Sample well
14 Withdrawal flange
15 Rinsing flange
16 Stop collar
17 Anti-rotation element
18 Sample container
19 Withdrawal device
20 Withdrawal tongs
21 Handle
22 Pressure rod
23 Pressure cone
24 Elastic sections
25 Collar-like step
26 Notch
27 Collar
28 Opening
29 Drip glass
30 Cover
31 Vertical axis
32 Line

The invention claimed is:

1. A device for collecting samples from a powder stream guided in a powder line (3), which device comprises a housing (1) that is disposed outside on the powder line (3) and that comprises a housing axis (6) extending radially relative to the longitudinal axis of the powder line (3), a slide (5) which is mounted for movement along the housing axis (6) and the end face (9) of which is located so as to be flush with the inner wall of the powder line (3) in the inoperative position of the slide and the circumference of which comprises a sample well (13) disposed upwardly relative to the powder stream, a pushing device that is suitable for moving the slide (5) along the housing axis (6) in such a way that the sample well (13) can be moved into the powder stream, the slide (5) comprising a surface (12) at least in the region extending from the sample well (13) to the end face (9), which surface (12) matches a corresponding opening in the powder line (3), characterized in that a sample container (18) is provided that can be supported in the sample well (13), and a withdrawal device (19) is provided which comprises withdrawal tongs (20) that can be inserted into the housing (1) in such a way that the withdrawal tongs (20) are located axially above the sample well (13) in the inoperative position of the slide (5) and can be fitted on the sample container (18) and connected to the same.

2. The device as defined in claim 1, characterized in that two spreadable elastic sections (24) are provided in the form of the withdrawal tongs (20) at the bottom front end of the withdrawal device (19), which two spreadable elastic sections (24) comprise a step (25) located centrally, and a pressure rod (22) is mounted for movement in the withdrawal device (19), at the bottom end of which pressure rod (22) there is a pressure cone (23) disposed that bears against the step (25) in the inoperative position.

3. The device as defined in claim 1, characterized in that a withdrawal flange (14) is provided on the housing (1), through which withdrawal flange (14) the withdrawal tongs (20) can be inserted up to the sample well (13).

4. The device as defined in claim 1, characterized in that a collar (27) is provided on the sample container (18) and notches (26) matching the collar (27) are provided on the elastic sections (24) in such a way that a sample container (18) can be held on the withdrawal tongs (20).

5. The device as defined in claim 3, characterized in that there is a cover (30) provided on the withdrawal flange (14).

6. The device as defined in claim 3, characterized in that there is a rinsing flange (15) provided downwardly on the housing (1).

7. The device as defined in claim 6, characterized in that the withdrawal flange (14) is connected to lines for the purpose of supplying liquid and/or gaseous rinsing agents, and the rinsing flange (15) is connected to a line for discharging liquid and/or gaseous rinsing agents.

8. The device as defined in claim 1, characterized in that there is a mechanical device provided, by means of which the withdrawal tongs (20) disposed on the withdrawal device (19) can take hold of the sample container (18) and manipulate the same into or out of the sample well (13).

\* \* \* \* \*